(12) United States Patent
French et al.

(10) Patent No.: US 7,084,314 B1
(45) Date of Patent: Aug. 1, 2006

(54) POLYCYCLIC FLUOROALKANES

(75) Inventors: Roger Harquail French, Wilmington, DE (US); Weiming Qiu, Wilmington, DE (US); Sheng Peng, Wilmington, DE (US)

(73) Assignee: E. I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/149,635

(22) Filed: Jun. 9, 2005

(51) Int. Cl.
*C07C 19/08* (2006.01)

(52) U.S. Cl. ..................................... 570/130
(58) Field of Classification Search ............... 570/130
See application file for complete search history.

(56) References Cited

U.S. PATENT DOCUMENTS 4,647,581 A    3/1987  Kolhl et al.

FOREIGN PATENT DOCUMENTS

| JP | 2005035941 A | * | 7/2003 |
| JP | 2005 035941 | | 2/2005 |

OTHER PUBLICATIONS

Mcbee et al., Diels-Alder Reactions with Fluorine containing Olefins, J. Amer. Chem. Soc., 1954, pp. 915-917, vol. 77.
J. March, Reactions, Mechanisms and Structure, Advanced Organic Chemistry, 4th Edition, 1992, pp. 598, 766 and 771.
Switkes et. al., Immersion Lithography at 157 NM. J. Vac. Sci. Technol. B. Nov./Dec. 2001, pp. 2353-2356, vol. 19 (6).
M. Switkes et. al., Resolution Enhancement of 157 NM Lithography by Liquid Immersion, Proc. Spie, 2002, pp. 459-465, vol. 4691.

* cited by examiner

*Primary Examiner*—Johann Richter
*Assistant Examiner*—Kellette Gale

(57) ABSTRACT

Polycyclic fluoroalkanes that are highly transparent to UV wavelengths ranging from about 190 nm to 260 nm are provided. The polycyclic fluoroallkanes are suitable for use in a variety of applications, particularly in the vacuum UV and deep UV region of the electromagnetic spectrum. For example, the polycyclic fluoroalkanes are useful in optical couplants, optical cements, optical elements, optical inspection media for semiconductor wafers and devices, and immersion photolithography, particularly at 193 and 248 nm exposure wavelength.

14 Claims, 4 Drawing Sheets

Wet. Immersion Fluid

Dry. Nitrogen Gas

POLYCYCLIC FLUOROALKANES

FIELD OF THE INVENTION

The present invention is directed to a novel class of polycyclic fluoroalkanes useful as solvents, cleaning agents, heat transfer fluids, refrigerants, lubricants, and, in preferred embodiments, optical applications in the vacuum ultraviolet (VUV).

BACKGROUND

McBee et al. *J. Amer. Chem Soc.* 77 pp 915–917 (1954) discloses Diels Alder addition of a fluorinated olefin to a cyclic diene to form less than 10% of a compound having the formula

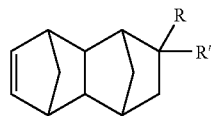

where R=H, $CF_3$, or $C_2F_5$; and R'=H or $CH_3$.

Koebl et al., U.S. Pat. No. 4,647,581 discloses 2-trifluoromthyl-2,3,3-trifluoro-1,2,3,4,5,8,9,10-octahydro-1,4:5,8-dimethanonaphthalene.

Catalytic hydrogenation of a double bond to a saturated structure is well known in the literature. (March J., *Advanced Organic Chemistry*, 4$^{th}$ Ed., 1992, p 771 and references therein).

Takashi et al., JP2005035941A, discloses the Pd/C— catalyzed hydrogenation of the double bond in

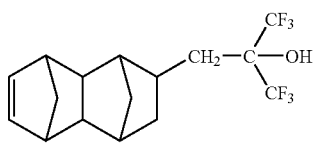

by bubbling room temperature hydrogen through the starting material for five hours at atmospheric pressure.

Immersion photolithography is described in Switkes et al, *J. Vac. Sci. Technol. B,* 19 (6), 2353 6, November/December 2001; and, M. Switkes et al, "Resolution enhancement of 157-nm photolithography at 157 nm exposure wavelength by liquid immersion", *Proc. SPIE* Vol. 4691, pp. 459–465 (2002). In immersion photolithography the optical source, the target surface, or the entire lithographic apparatus is immersed in a highly transparent high refractive index liquid. Realization of the potential benefits of this technology is dependent upon identifying liquids with exceptionally high transparency in the VUV/DUV with excellent photochemical stability. The present invention is directed to these, as well as other, important ends.

SUMMARY OF THE INVENTION

One aspect of the present invention is a polycyclic fluoroalkane represented by the formula

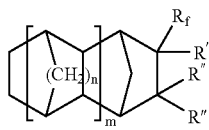

where $R_f$ is a fluorinated alkyl of 1–10 carbons that is linear, branched, or cyclic; R' is H, F, an alkyl of 1–10 carbons that is linear, branched, or cyclic; a fluorinated alkyl I of 1–6 carbons that is linear, branched, or cyclic; each R" is independently H or F; n=0 or 1; and, m=1 or 2 provided that m is not 2 when n=0.

Another aspect of the present invention is a composition comprising a compound represented by the formula

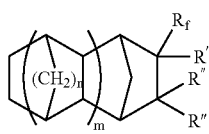

where $R_f$ is a fluorinated alkyl of 1–10 carbons that is linear, branched, or cyclic; R' is H, F, an alkyl of 1–10 carbons that is linear, branched, or cyclic; a fluorinated alkyl I of 1–6 carbons that is linear, branched, or cyclic; each R" is independently H or F; n=0 or 1; and, m=1 or 2 provided that m is not 2 when n=0, and having a concentration of oxygen below 1 ppm.

These and other aspects of the invention will be apparent to those skilled in the art, in view of the following disclosure and the appended claims.

DETAILED DESCRIPTION

Figure 1:
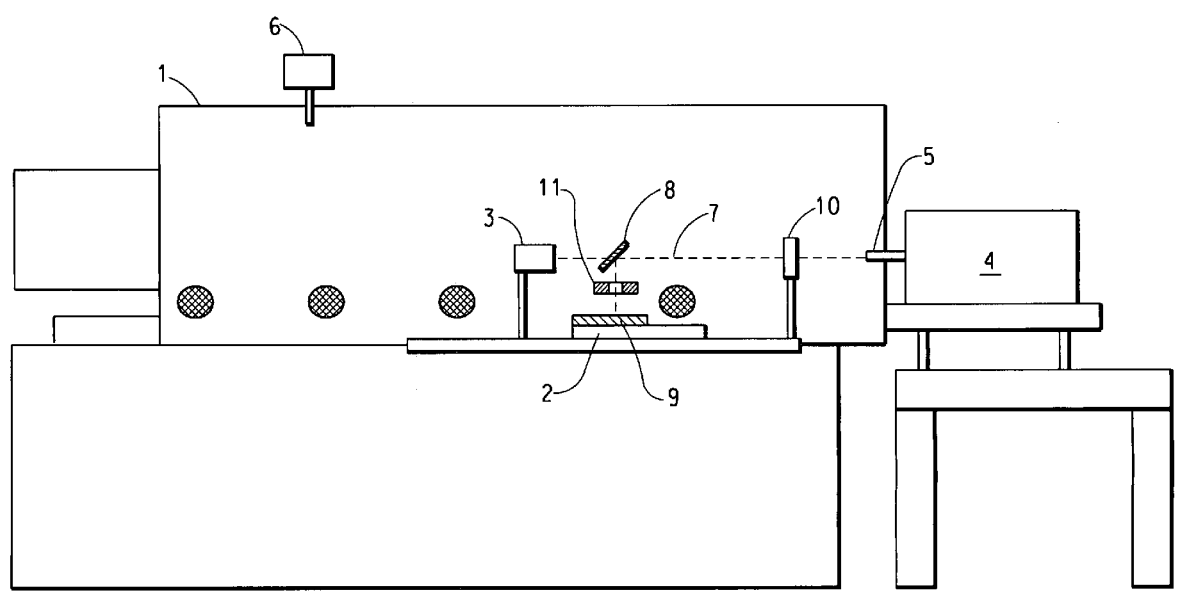
FIG. 1 shows an example of equipment for immersion contact lithography.

In preferred embodiments, the polycyclic fluoroalkanes disclosed herein are of sufficient purity to be useful in applications such as immersion photolithography. The term "purity", as used herein with regard to preferred purity for use in application such as immersion photolighography, refers to purity as indicated by spectroscopic absorbance at 193 nm. For example, a polycyclic fluoroalkane having a chemical purity of 99%, and contains 1% non absorbing impurities and a total of about 1 ppm or less of one or more absorbing impurities, the polycyclic fluoroalkane is expected to be suitable for use in immersion lithography.

However, a polycyclic fluoroalkane having a chemical purity of 99.9% and containing 0.1% of absorbing impurities may not be suitable for use in immersion lithography.

In some preferred embodiments, the polycyclic fluoroalkanes are not present in the form of single isomers, but can comprise three or more isomers.

The processes for preparation of the preferred polycyclic fluoroalkanes of the present invention include removing UV absorbing olefinic residues and trace organic contaminants.

The present invention provides polycyclic fluoroalkanes useful as solvents, cleaning agents, lubricants, and optical transmission media. The polycyclic fluoroalkanes are also expected to be useful in other applications for which optical purity, e.g., minimal absorbance in the ultraviolet region of the electromagnetic spectrum and particularly at 193 nm, is desired.

In one embodiment of the present invention there is provided a polycyclic fluoroalkane compound represented by the formula

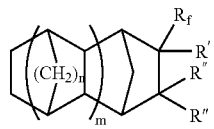

I where $R_f$ is a fluorinated alkyl radical of 1–10 carbons that can be linear, branched, or cyclic; R' is H, F, an alkyl radical of 1–6 carbons that is linear, branched, or cyclic, or a fluorinated alkyl radical, of 1–6 carbons that can be linear, branched, or cyclic; each R" is independently H or F, n=0 or 1, and m=1 or 2 provided that m is not 2 when n=0.

In a preferred embodiment, n=1, m=1, $R_f$ is perfluoromethyl or perfluoroethyl, and R' is H or F. Most preferably $R_f$ is perfluoromethyl. In a preferred embodiment, the molar ratio of fluorine to hydrogen, F/H is less than 0.5, but greater than zero.

One of skill in the art will appreciate that several stereoisomers of polycyclic fluoroalkanes represented by the formula I are possible. Such isomers are intended to be within the scope of the present invention.

As used herein, the term "F/H ratio" is employed to characterize the polycyclic fluoroalkanes. The F/H ratio is determined by dividing the number of carbon-fluorine bonds by the number of carbon-hydrogen bonds. For polycyclic fluoroalkanes according to the present invention the F/H ratio is greater than zero.

In a preferred embodiment the polycyclic fluoroalkane has an F/H ratio of 0.5 or less, but greater than zero. Such polycyclic fluoroalkanes have been found to have surprisingly high suitability for use in applications requiring transparency in the vacuum ultraviolet (VUV), including in condensed phase optical components such as optical adhesive compositions, solvents for pellicle polymers, index matching fluids and the like. Of particular note is the suitability of the polycyclic fluoroalkanes in the emerging field of immersion photolithography in the VUV, particularly at 193 nm. In immersion photolithography, a process used for the fabrication of microcircuits as described in Switkes et al., op.cit., a target surface is partially or wholly immersed, preferably wholly immersed, in a medium of high transparency and higher refractive index than air or other gaseous atmospheres.

The terms "imaging," "imaging applications," "image-wise", as used herein, refer to formation of an image on a substrate by disposing a polycyclic fluoroalkane between a light source and an illuminated surface such that at least a portion of the emitted light illuminating the surface is caused to be transmitted through the polycyclic fluoroalkane.

Unless otherwise stated, concentrations expressed herein as parts per million (ppm) refer to parts per million by weight on the basis of the total weight of the composition referred to.

When an amount, concentration, or other value or parameter is recited herein as either a range, preferred range or a list of upper preferable values and lower preferable values, the recited amount, concentration, or other value or parameter is intended to include all ranges formed from any pair of any upper range limit or preferred value and any lower range limit or preferred value, regardless of whether such ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The term "heart cut" is used herein in reference to a fractional distillation, to refer to that portion of a condensate that is collected when the temperature of the condensate has reached a plateau.

The term "oxygen-minimized", as used herein, means that steps are taken to reduce the contamination by atmospheric oxygen of the suitable polycyclic fluoroalkane. In preferred embodiments, dissolved oxygen is undesirable because it can poison the performance of a polycyclic fluoroalkane at vacuum ultraviolet wavelengths in sensitive optical applications such as immersion lithography employed for the preparation of microcircuits.

The preferred polycyclic fluoroalkanes have an F/H ratio of 0.5 or less, but greater than zero, a refractive index of 1.50 or greater, and an absorbance at 193 nm of 2.0 cm$^{-1}$ or less It is known that the addition of fluorine to a hydrocarbon often results in the reduction of refractive index. It is further known that many fluorinated materials exhibit excellent transparency in the infrared, but not the vacuum ultraviolet. It is also known that increasing the carbon to hydrogen ratio in hydrocarbons, typically by employing cyclic structures, has the effect of increasing refractive index although normally at some cost in transparency. However, unsaturated or functional group containing structures are generally not well suited for use in the vacuum ultraviolet.

The inventors have found surprisingly that a balance of desirable properties for VUV immersion photolithography applications can be achieved by employing polycyclic fluoroalkanes having an F/H ratio of less than 0.5; that is, by employing saturated polycyclic hydrocarbons in which on a mole-% basis, only about one third or fewer of the hydrogens are replaced by fluorines.

The transparency and high photochemical stability of the preferred polycyclic fluoroalkane makes them suitable for use in immersion photolithography in the vacuum ultraviolet/deep ultraviolet (VUV/DUV) region of the electromagnetic spectrum. However, it is desirable that steps be taken to maintain purity of the processes, materials, and equipment used throughout the preparation, purification, and handling of the polycyclic fluoroalkanes because advanced optical applications such as immersion lithography in the VUV are extremely intolerant of contaminants. For example, olefins are sources of photochemical instability, and increase absorbance tremendously. Oxygen is a source of photochemical instability, and long-term storage problems deriving therefrom. It is desirable to minimize the presence of both olefins and oxygen during the processes disclosed herein.

One advantageous method for the preparation of the polycyclic fluoroalkanes is to hydrogenate a polycyclic fluoro-olefinic precursor represented by the structure

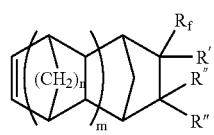

II where m, n, $R_f$, R', and R" are as described hereinabove. The olefinic precursor II can be prepared by the well-known Diels-Alder reaction of a fluorinated olefin with a cyclic diene. The reaction can advantageously be performed at a temperature of about 200° C. for about 48 hours, according to the methods described in McBee et al. *J. Amer. Chem Soc.* 77 pp 915–917 (1954), the disclosures of which are hereby incorporated herein by reference in their entirety.

Hydrogenation of the double bond in the compound of formula (II) can be accomplished by processes known to those skilled in the art, such as that of Takashi et al, cited hereinabove. However, because of the criticality imposed by preferred uses of the polycyclic fluoroalkanes, it is desirable to achieve the highest possible conversion of olefin to alkane, preferably leaving only trace amounts of olevin for removal during further purification. Hydrogenation in a sealed vessel has been found to be highly effective for the preparation of pure polycyclic fluoroalkanes of Structure I from the olefinic precursor of Structure II. In a preferred process, conversion is effected under a gradually increasing pressure of hydrogen and gradually increased temperature.

In a preferred embodiment, the hydrogenation is carried out in the temperature range of 0–250° C., preferably 0–150° C. The hydrogen pressure can be in the range from atmospheric pressure to 2,000 psig, preferably from atmospheric pressure to 600 psig.

In a preferred embodiment, the reaction is carried out in a sealed pressure vessel such as an autoclave. Reaction is preferably started at room temperature under 1–50 psi, preferably 20–50 psig hydrogen pressure. The autoclave is repressurized with hydrogen to 50 psig pressure when the internal pressure drops to about 0 psig. When it is observed that the hydrogen consumption rate is beginning to decrease—typically after about 20 to 30 minutes—the hydrogen pressure is increased to 200 psig and maintained at 200 psig for about 15 minutes. The autoclave is preferably shaken or the contents otherwise agitated. The reaction temperature is increased to 150° C. over a period of about 75 minutes, and then the hydrogen pressure is increased to 600 psig. The reaction is continued under these conditions (150° C. and 600 psig pressure hydrogen) for about 2 hours.

While it is not intended that the present invention be bound by any particular theory, it is believed that, from the standpoint of conversion, as much as 99% conversion occurs in the first twenty to thirty minute stage of reaction at room temperature under less than 50 psig hydrogen pressure. The subsequent elevation of hydrogen pressure and temperature and prolonged reaction time are intended to push the reaction to completion. It is estimated that conversion of greater than 99.5% can be achieved.

The hydrogenation can be carried out using the neat liquid olefin of formula II or, preferably, with the olefin dissolved in organic solvents, such as methanol, ethanol, propanol, isopropanol, butanol, acetonitrile, acetone, acetic acid, ethyl acetate or combinations thereof. It is preferred to run the reaction in methanol, ethanol, acetone, or ethyl acetate solution at a concentration of 30 to 80%.

Because of the need for purity, it is highly preferred to employ a heterogeneous catalyst so that it can be filtered out. Many heterogeneous catalysts are suitable for use, such as palladium-on-charcoal, Raney nickel, Raney cobalt, platinum metal or its oxide, rhodium, ruthenium and zinc oxide. Homogenous catalysts, such as chlorotris(triphenylphosphine)rhodium, can also be used.

In preferred embodiments, the polycyclic fluoroalkanes having a F/H ratio of 0.5 or lower are suitable for use as an immersion fluid in liquid immersion photolithography for the preparation of microcircuits. A preferred polycyclic fluoroalkane is represented by the structure III,

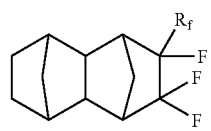

III where $R_f$ is perfluoromethyl or perfluoroethyl.

In order to maximize the utility of a polycyclic fluoroalkane in optical applications in the VUV, particularly in immersion photolithography, the polycyclic fluoroalkane is treated to ensure that oxygen concentration in the polyclic flouroalkane does not exceed 2 parts per million by weight (ppm). The polycyclic fluoroalkane is also preferably treated to remove trace organic contaminants. A so-treated polycyclic fluoroalkane exhibits absorbance of less than 2.0/cm, preferably 0.1 to 1.0 cm$^{-1}$, at 193 nm. In a most preferred embodiment of the present invention, the oxygen concentration of the polycyclic fluoroalkane after treatment to remove oxygen and trace organic contaminants does not exceed 1 ppm.

The inventors have found that the VUV absorbance of the polycyclic fluoroalkanes can be reduced significantly with further treatment. Outlined herein are suitable methods for purifying the as-prepared polycyclic fluoroalkanes. As will be understood by one skilled in the art, not all of the methods of purification will be necessary, but generally, some combination of methods is desirably used to effect the desired degree of absorbance.

Certain organic impurities, such as olefins, substituted cycloalkanes, branched alkanes, oxidation products such as peroxides and ketones, and the like may be present. Some organic impurities are orders of magnitude more absorbing than other organic impurities. For example, a suitable polycyclic fluoroalkane contaminated by a percent or two of cyclobutane, which is quite transparent though of high vapor pressure and low refractive index, may be suitable for use in the processes disclosed herein. On the other hand, it may be desirable that the concentration of more highly absorbing contaminants, such as olefins and carbonyls, is on the order of 1 ppm or even less.

Highly absorbing contaminants can be removed from the polycyclic fluoroalkane by such methods as fractional distillation, sparging, freeze-thaw cycling, zone refining, treatment with concentrated sulfuric acid or oleum, and treatment with adsorbents such as silica, molecular sieves of various pore sizes, carbon, silica gel, alumina, or mixtures thereof.

Preferably, the polycyclic fluoroalkane exhibits absorbance at 193 nm of 0.1 to 1.0 cm$^{-1}$. One of skill in the art will appreciate that the absorbance is preferably as low as possible, provided the oxygen concentration is desirably low. It will be appreciated by one of skill in the art that at purity levels required to achieve this result, the most sensitive measurement of contamination is the spectroscopic absorption itself. In other words, the best way to tell that the most important impurities have been removed is to measure the absorbance. Absorbance below 1 cm$^{-1}$ is by far the most sensitive available indicator of purity in regard to trace amounts of absorbers in the polycyclic fluoralkanes.

The term "absorbance" refers to two related phenomena. On the one hand, the term "absorbance" refers to the actual absorbance of the polycyclic fluoroalkane in actual use in the processes disclosed herein, which can be affected by external influences such as the solubility of a photoresist, as discussed hereinabove. On the other hand, "absorbance" also refers to the analytical spectroscopic method employed to determine absorbance under laboratory conditions. The latter is a highly desirable method for evaluating the concentration of contaminating adsorbents in compositions of high purity.

It may be desirable to first subject the as-prepared polycyclic fluoroalkane to fractional distillation in the cleanest possible, preferably grease-free, distillation apparatus. The heart cut of the distillate thus produced is then mixed in the liquid state with of concentrated sulfuric acid or oleum followed by separation from concentrated sulfuric acid or oleum neutralization, washing with water, and distillation. This distillate thus produced is then mixed in the liquid state with an adsorbent or preferably a mixture of two or more adsorbents, which can include, for example, silica gel, 3A, and 5A zeolite molecular sieves, alumina, and/or activated carbon. All subsequent handling of the thus purified polycyclic fluoroalkane is then desirably performed in an oxygen-minimized atmosphere, preferably an inert gas atmosphere, most preferably a helium or nitrogen atmosphere. This includes the use thereof in immersion photolithography, which is preferably performed in an oxygen-minimized atmosphere.

Concentrated sulfuric acid or oleum treatment is used before adsorbent treatment. The amounts of concentrated sulfuric acid or oleum for such treatment is dependent on the impurity level in the fluids to be treated. In most cases 2 to 30% by volume of concentrated sulfuric acid or oleum is used, although more concentrated treatments can be used. It is preferred to use 5 to 15% concentrated sulfuric acid or oleum by volume to treat the polycyclic fluoroalkane at room temperature. Before treating the polycyclic fluoroalkane with adsorbents, the used concentrated sulfuric acid or oleum is removed by layer separation, neutralization, and washing with water.

Silica gel and zeolite adsorbents are most effective if activated, preferably by heating while purging with a dry gas flow. It is preferable that adsorbent activation be done immediately prior to use. Activation can be achieved by heating to about 200 to 500° C. under a flow of dry, pure air, nitrogen, or helium for several hours. Air at 500° C. has the advantage of burning most residual organic contaminants off an adsorbent such as a silica gel or a zeolite. The gas flow can be continued as the system cools down to a temperature in the range of room temperature to 100° C. In an alternative procedure the gas flow is stopped and the system sealed off.

In another alternative procedure, the gas flow is stopped and the system evacuated as the adsorbent cools to a temperature in the range of room temperature to 100° C. The advantage of stopping the gas flow while the adsorbent is at 500° C. is that this minimizes recontamination from any adventitious impurities in the gas as the adsorbent cools down.

A preferred method of activating the silica gel and zeolite adsorbents is the following. A Hastelloy® tube in a clamshell furnace is loaded with adsorbent and then heated under an air flow for two hours at 500° C. The airflow is stopped and the Hastelloy tube immediately sealed at both ends. Once the sealed Hastelloy® tube has cooled to room temperature, it is transferred to a $N_2$ glove bag where the tube is opened and the adsorbent added to a bottle containing suitable polycyclic fluoroalkane liquid that is to be purified. Although the ratio of adsorbent to liquid can be varied without limit, it has been found satisfactory to employ one volume of adsorbent for every 1 to 20 volumes of liquid. The actual amount of adsorbent required will depend upon the level of contamination in the as-received liquid. It is therefore well advised to employ some excess to insure maximum effectiveness in removal of contaminants.

A key aspect of any distillation process employed in the purification of the polycyclic fluoroalkane is that it be performed in the cleanest, least contaminated distillation apparatus possible. It is particularly desirable to exclude oxygen and any adventitious or systemic organic contaminants. It is found in the practice of the invention that employment of grease, including fluorinated greases, such as are commonly employed in distillation and vacuum systems to provide improved sealing and easier part removal can contaminate the distillate herein sufficiently to actually degrade the absorbance. It is therefore highly preferably to perform the distillation in a "grease-free" distillation system. "Grease-free", as used herein, means that no grease is employed when assembling the cleaned parts of the system. One of skill in the art will appreciate that the term "grease-free" does not mean that the invention is not operable should there be some small amount of grease contamination somewhere in the system. To the extent that the system can be cleaned of all grease contamination, the absorbance is advantageously reduced, but "grease-free" is not intended to require the complete absence of any grease in no matter how small a concentration.

There are numerous uses for the highly transparent polycyclic fluoroalkanes in the VUV. Contemplated applications include, but are not limited to, optical couplants, optical cements, optical elements such as liquid lenses, index-matching optical inspection media for semiconductor wafers and devices, and immersion fluids, especially for 193 and 248 nm photolithography. In highly preferred embodiments, particularly for optical applications, the polycyclic fluoroalkanes have an F/H ratio of $\leq 0.5$, but greater than zero, and a refractive index in the range of 1.5 to 1.7, more preferably 1.6 to 1.7.

Sparging is a suitable method for removing contaminants from the polycyclic fluoroalkanes, particularly for the removal of oxygen. One method for sparging that can be used is as follows: A glove box is supplied with dry, low-oxygen-content nitrogen such as 99.998% or better nitrogen sold as a cylinder gas by Matheson or by the boil-off of liquid nitrogen. A liquid aliquot of about 10 ml of the polycyclic fluoroalkane is placed in a 20 ml glass scintillation vial. The sample is transferred into the nitrogen purged dry box. The vial is secured flat on the work surface; the plastic cap is removed from the vial, a disposable glass pipette lowered into the solvent and then nitrogen delivered via the pipette from the same dry, low-oxygen source as the glove box. Flow rate is adjusted to maintain vigorous bubbling of solvent short of causing the solvent to splash out of the vial. Vigorous sparging is continued for 30–60 seconds, long enough to significantly decrease oxygen content and possibly water content without major loss of the polycyclic fluoroalkane to evaporation. Because available instrumentation has a sensitivity limit of about 1 ppm of oxygen the actual oxygen concentration in a specimen may be considerably lower than 1 ppm, Henry's Law can be employed to estimate the oxygen concentration, using Henry's Law constants available in the literature. Based upon such estimates, it is estimated that the actual oxygen concentration in the polycyclic fluoroalkane hereof when handled in an oxygen-minimized atmosphere is less than 100 ppb (parts per billion).

The nitrogen atmosphere in which the specimens were handled in the specific embodiments in the Examples below was produced from boiled off liquid nitrogen and is estimated to have had an oxygen concentration of 3–5 ppm.

An alternative method for purifying the polycyclic fluoroalkanes is bulb-to-bulb distillation through a bed of 3 Å molecular sieves. For example, two flasks are connected by a tube containing 3 Å molecular sieves preheated as described above. One of the flasks is then partially filled with the liquid that is to be purified and the system resealed. The liquid is subjected to three freeze/thaw cycles to remove dissolved oxygen. The system is then thoroughly evacuated after refreezing the liquid with liquid nitrogen. The system is sealed under vacuum and the liquid nitrogen cooling bath transferred from the flask containing the liquid to the empty flask. As the liquid warms towards room temperature it distills through the bed of 3 Å molecular sieves to the chilled flask. Once distillation is complete the vacuum is relieved with oxygen free nitrogen, the purified liquid allowed to warm to room temperature, and the flask then sealed for subsequent use.

From the standpoint of practical utility, it is highly desirable to remove contaminating species that exhibit photochemical reactivity. Such species not only tend to be strongly absorbing in the wavelength region from 190 to 260 nm, but also can undergo photo-induced reactions, often resulting in bubble formation and darkening. Extraction of any one photochemically active species is beneficial whether or not any other photochemically active species present is extracted.

According to one embodiment, a surface is imagewise exposed to electromagnetic radiation in the wavelength range of 190–260 nm, preferably at 193 nm and 248 nm. In preferred embodiments, the entirety of a surface is illuminated by the emitted light. Preferably, for some applications, the surface is exposed in a pattern, leaving some portions exposed and others not. Preferably the surface is fully immersed in the polycyclic fluoroalkane.

In preferred embodiments, the polycyclic fluoroalkanes are suitable for use in immersion photolithography in the wavelength range from 190 to 260 nm, preferably at 193 nm or 248 nm, most preferably at 193 nm. In such applications, at least the photoresist target surface is immersed in the polycyclic fluoroalkane. A liquid suitable for use in immersion photolithography is preferably transparent enough to allow a working distance of at least 10's of micrometers and have radiation durability, i.e., the liquid can withstand intense irradiation at 193 nm substantially without damage. The combination of transparency, refractive index, and radiation durability of the polycyclic fluoroalkanes hereof makes them particularly well suited for immersion photolithography at 193 nm exposure wavelength.

It is also highly preferred that the suitable polycyclic fluoroalkanes be chemically and physically compatible with other materials used in the photolithographic process. In immersion photolithography at 193 nm exposure wavelength, the immersion fluid is in contact with a photoresist polymer. It is highly desirable that the immersion fluid not dissolve or swell the photoresist, not interfere with latent image formation in the photoresist under 193 nm exposure, and not interfere with subsequent development of the photoimaged photoresist in a developer solution. In addition the immersion fluid preferably has a low enough volatility that it does not require a pressure vessel for containment and can be removed for reprocessing prior to post exposure baking and development.

To prevent the immersion fluid from damaging the resist, depending upon the composition of the immersion fluid, a topcoat may be necessary, as described hereinabove. A suitable topcoat is preferably substantially transparent in the range of 190–260 nm wavelength, particularly at 193 and 248 nm, photochemically inert in that wavelength range, substantially insoluble in the polycyclic fluoroalkane, and soluble in solvents in which, the photoresist is insoluble. In a typical process, the substrate is spin-coated with a photoresist, a selected top-coat polymer is dissolved in a suitable solvent, the photoresist-coated substrate is spin-coated with a topcoat, and the spin-coated substrate is contacted with the polycyclic fluoroalkane. Photoimaging can then be carried out, the topcoat removed by dissolution in a solvent that does not dissolve or swell the photoresist, and the photoresist developed according to methods known to those skilled in the art.

In some processes, the preferred polycyclic fluoroalkane is subject to repeated exposure of intense bursts of laser light, and is in contact with other surfaces that, however, clean, may still contain some contamination. Both these effects can be deleterious over time to the absorbance of the polycyclic fluoroalkane. The polycyclic fluoroalkane can be restored to absorbance below 1 $cm^{-1}$ by recycling through adsorbents such as those recited hereinabove, preferably under inert gas. Recycling and regeneration of the polycyclic fluoroalkane can be accomplished batch-wise or continuously.

In the typical practice of immersion lithography, it is anticipated that 193 nm radiation from an ArF excimer laser is transmitted through a photomask, typically comprising a chrome metal circuit diagram patterned on glass, forming an image of the circuit pattern on a photoresist. Numerous materials for use as photoresists are well known in the art and are in widespread commercial use. All such materials are suitable for use with the polycylic fluoroalkanes, so long as they are sensitive 193 nm light, i.e., optically absorbing and able to capture a latent image upon irradiation, and are substantially insoluble in the polycyclic fluoroalkane or can be protected from dissolution by a topcoat. Suitable photoresist compositions are disclosed in *Introduction to Microlithography*, Second Edition by L. F. Thompson, C. G. Willson, and M. J. Bowden, American Chemical Society, Washington, D.C., 1994. Examples of suitable photoresists include the 193 nm Epic® resists from Rohm and Haas Electronic Materials, (Marlborough, Mass.), and similar resists from companies such as TOK (OHKA AMERICA, INC. Headquarters/Hillsboro, Oreg. or AZ Electronic Materials, Somerville, N.J.

Both positive-working photoresists, such as Rohm and Haas's Epic 2200 and negative-working photoresists such as Rohm and Haas's UVN30 resist are suitable for use in the immersion photolithography process. A positive-working photoresist is one wherein the regions exposed to light are rendered soluble in the developer while the unexposed regions are insoluble therein. A negative-working photoresist, is one wherein the regions exposed to light are rendered insoluble in the developer while the regions unexposed to light are soluble therein.

A photoresist, when imagewise exposed to light, forms what is called a latent image. In one embodiment of a process of the invention, a chemically amplified, positive resist containing a photoacid generator (PAG), is employed. The photoresist layer comprising the latent image is subject to a post exposure bake (PEB) step for typically 60 seconds at temperatures between 90 and 140 C in air. After this PEB step, the photoresist coated wafer is then put into an aqueous base developer, such as a 0.26 Normal TMAH developer, whereby the exposed regions of the polymer film are developed away, and the patterned photoresist is observed.

While there is no particular limitation on the thickness of the photoresist layer, typically, for use in the processes disclosed herein, the photoresist coating is 150 nm to 200 nm in thickness on a silicon wafer substrate. The desired thickness is determined by the desired minimum feature sizes to be printed. For the purpose of illustration of this concept, but in no way limiting on the scope of the invention, using an aspect ratio of 3–4, a typical value in the semiconductor art, if the desired features are 65 nm in width, the film thickness should be ~195 nm. In general, the thicker the photoresist layer, the better resistance to dry etch processes in subsequent processing of the patterned photoresist layer.

It is desirable that the presence of a topcoat does not materially alter the operability of immersion photolithography. Suitable topcoats include, but are not limited to, highly transparent fluoropolymers, which are soluble in fluorinated solvents, which fluorinated solvents in turn are not solvents for the photoresist polymers. Particularly preferred are amorphous perfluoropolymers such as Teflon® TFE-AF, available from DuPont. In a typical application, an amorphous fluoropolymer is dissolved to a concentration of 1–5% by weight in a perfluorinated solvent such as Fluorinert™ FC-75. The solution so formed is spin-coated onto a photoresist coated substrate to form a topcoat film of 50–300 nm thickness.

One of skill in the art will appreciate that the source of the 193 nm radiation, or radiation in the wavelength range of 170–260 nm, is not critical. ArF excimer lasers are convenient, controllable, high intensity sources of 193 nm radiation and are therefore preferred.

Figure 2:
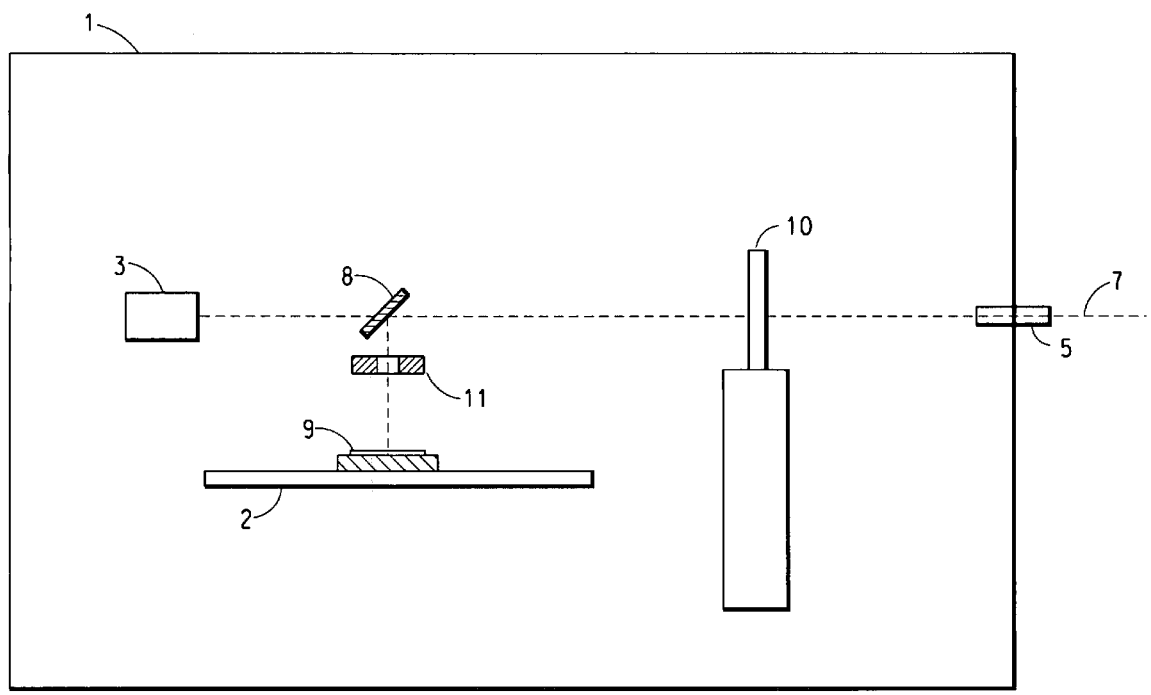
FIG. 2 shows optical apparatus for immersion contact lithography according to one embodiment of the invention.
Figure 3A:
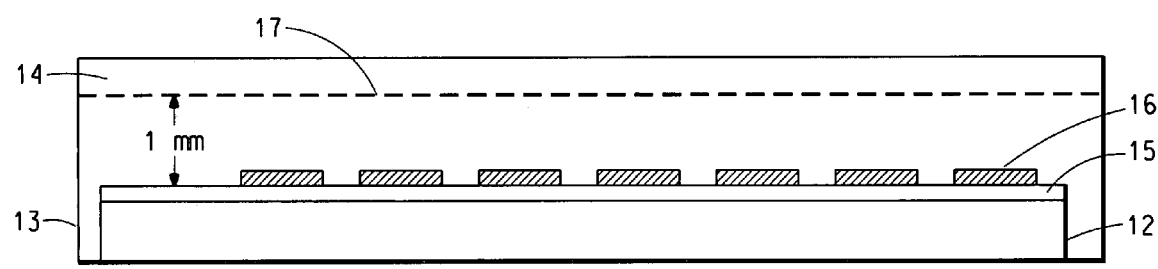
FIG. 3 shows the wafer exposure stage for immersion contact lithography according to one embodiment of the invention.
Figure 3B:
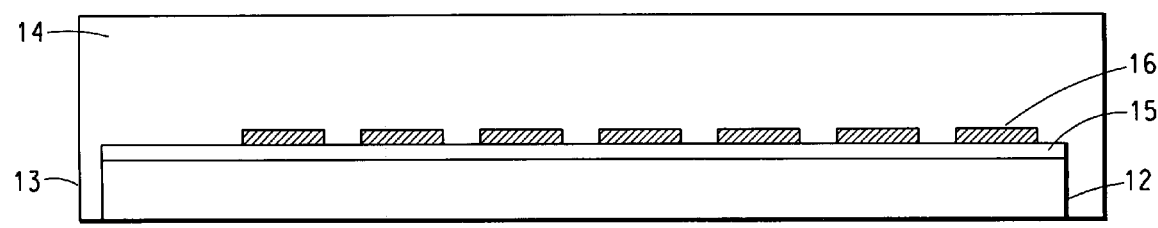

One embodiment of a photolithographic process according to the invention is depicted in FIGS. 1,2 and 3. FIG. 1 shows a complete system, parts of which are advantageously disposed in a nitrogen dry box, 1, with an optical table, 2, mounted inside the dry box to accommodate optical components and a translating sample stage. A Scientech power meter, 3, is used to read the energy of the 193 nm laser light pulses emitted by an ArF excimer laser, 4. In the particular embodiment depicted in FIG. 1, the photolithographic exposure chamber is a low oxygen/low moisture nitrogen flushed dry-box (Nexus Dry Box, Vacuum Atmospheres Co., Hawthorne Calif. 90250-6896) adapted for use in the apparatus therein depicted. The 193 and 248 nm laser light is introduced into the dry box through an access port 5. A dry box control panel mounted built-in oxygen and moisture analyzer, 6, is used to monitor the oxygen content in the dry box, and to indicate when oxygen concentration has decreased to acceptable levels after introduction of samples. Upon introduction into the dry box chamber, the laser beam 7 is reflected downwards by a fused silica beam splitter, 8, to the photoresist coated silicon wafer, 9. The photoresist coated wafer is contained in a machined aluminum wafer holder and immersed to a depth of about 1 mm in the polycyclic fluoroalkane hereof. The whole plate can be translated under the laser beam to allow sequential exposures of different portions of the wafer, with differing exposure doses.

FIG. 2 shows more details of the optical exposure system of FIG. 1. The pulsed laser beam, 7, from the excimer laser 4 enters the dry box, 1, at the access port, 5, goes through a manually operated shutter, 10, and is then incident on a fused silica beam splitter 8, that reflects a small portion of the laser energy down towards the photoresist coated silicon wafer 9 mounted on a translator that allows the wafer to be translated under the laser beam. The majority of the laser beam continues through the beam splitter 8 and is then incident on a power meter head, 3.

Figure 4:
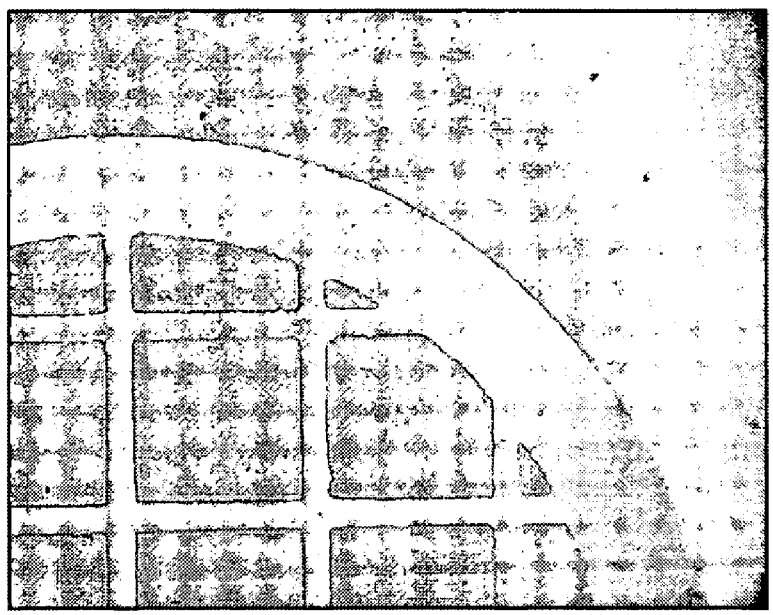
FIG. 4 shows a photograph of a photoresist image prepared using a polycyclic fluorohexane according to one embodiment of the invention.
Figure 5:
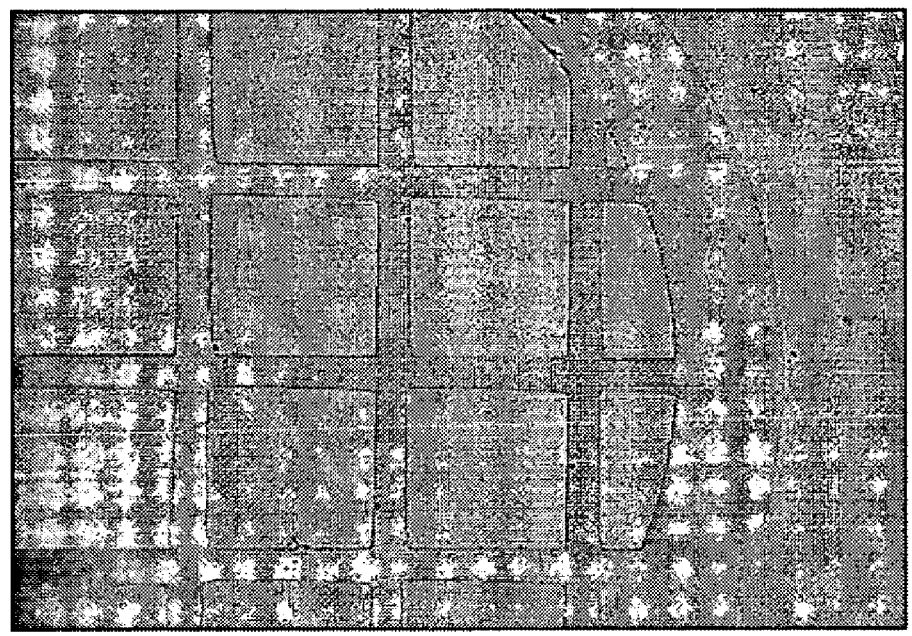
FIG. 5 shows a photograph of a photoresist image prepared without the use of an immersion fluid, according to one embodiment of the invention.

FIG. 3 shows the wafer exposure stage, where the laser light, from the excimer laser hits the silicon wafer 11, in the machined aluminum plate 12 that moves under the laser beam along the translation stage on the optical table 2 of FIG. 1, so as to permit the sequential exposures, at various exposure doses. 13 is the N2 environment of the N2 dry box. Desirably, the silicon wafer 11 has been coated with a photosensitive photoresist polymer 14 as discussed in more detail below. Not shown is the topcoat layer as hereinabove discussed. Depicted in FIG. 4 is an embodiment of contact immersion photolithography at 193 nm exposure wavelength wherein a photomask 15 is placed on the surface of the photoresist polymer layer and the immersion fluid is introduced to cover the photoresist coated silicon wafer to a depth of approximately 1 mm 16. It has been found that when the photomask is small and light, as for example the metal grids used in the examples herein, it is convenient to introduce the immersion fluid first and then to position the photomasks in the fluid and on the surface of the photoresist coated silicon wafer. FIG. 5 depicts the same set-up but without the immersion fluid; FIG. 5 is not an embodiment of the present invention.

The desired thickness of the polycyclic fluoroalkane layer is determined by the details of the imaging system being developed or used. For example, in contact photolithography at 193 nm exposure wavelength a suitable thickness of the polycyclic fluoroalkane immersion layer is 1 mm. A 1 mm thickness may also be suitable for scanning or stepping the wafer under a projection lens, while maintaining sufficient distance between the output element of the projection lens and the wafer. One of skill in the art will appreciate that as the immersion fluid thickness is increased attenuation of the light will also increase, but tolerances in regard to the mechanics of stepping and scanning may become easier. Thinner immersion liquid layers may permit higher light exposure levels, but with higher tolerances (e.g., about 1 mm) desired for achieving scanning and/or stepping the wafer at high speed and with high accuracy.

The polycyclic fluoroalkanes provide flexibility in system design, reducing the need to trade-off between the thickness of the immersion layer and mechanical design.

The polycyclic fluoroalkanes can be employed in a variety of other applications. Examples of other applications include those in which the polycyclic fluoroalkane is disposed between a VUV light source and a target. The polycyclic fluoroalkane can be employed neat, as in liquid lenses, index matching fluid, and the like, or it can be an ingredient of a mixture or a diluent, such as a solvent for polymers in spin-coating operations, a plasticizer in a polymeric film, or a solvent in an adhesive formulation.

In another embodiment, the polycyclic fluoroalkane can be used in optical inspection of patterned or unpatterned objects such as semiconductor wafers, where small size defects of varying optical properties are to be detected. The use of the polycyclic fluoroalkanes as immersion fluids for immersion inspection enables both higher resolution imaging in the inspection, and also reduces optical scattering from the topography of the sample, permitting the inspection of, for example, deep holes that may have defects, such as particulate debris, present. In still further embodiments, the polycyclic fluoroalkanes are useful in the fabrication of sheets, layers, coatings, and films used in lenses, light guides, anti-reflective coatings and layers, windows, protective coatings, and glues suitable for use in VUV photolithography.

The polycyclic fluoroalkanes can also be used in elements in a compound lens designed to reduce chromatic aberrations. Heretofore, only CaF2 and possibly hydroxyl free silica have been viewed as having sufficient transparency at 193 nm to be used in transmissive focusing elements. It is also known, as disclosed in, for example, R. Kingslake, Academic Press, Inc., 1978, Lens Design Fundamentals, p. 77, that by using a second material of different refractive index and dispersion, an achromatic lens can be created.

The present invention is further illustrated by, but not limited to, the following examples.

EXAMPLES

Methods

Optical Absorbance Measurements

The transmission based absorbance measurements were made using a Harrick Scientific Corp. (Harrick Scientific Corporation 88 Broadway Ossining, N.Y.) Demountable Liquid Cell model DLC-M13. The cell had a 8 mm aperture, which included two 13 mm diameter×2 mm thick $CaF_2$ windows, Viton® polymer o-ring seals, (2) Luer-Lok® fittings for loading sample, assorted Teflon® TFE spacer thicknesses from 6 micrometers to 4000 micrometers. The DLC-M13 was mounted in a variable angle spectroscopic ellipsometer manufactured by J. A. Woollam Co., Inc., Lincoln, Nebr., either a VUV-Vase® model VU-302 for measurements from the near IR to 145 nm, or a DUV-Vase® model V—for measurements from the near IR to 187 nm. The liquid specimen to be tested was held in a cell formed between parallel CaF2 windows by insertion of a Teflon® tetrafluoroethylene (TFE) ring between the windows. Teflon® TFE rings of 6, 25, 100, 500, 920, 2200, 3000, 4000, 6000, and 10000 micrometer thicknesses were used, providing multiple optical path lengths through different aliquots of the same sample. While charging the cell, care was taken to avoid bubbles in the 8 mm diameter window aperture.

The optical absorbance, A ($cm^{-1}$), is defined for purposes herein as the base 10 logarithm of the ratio of the transmission of the $CaF_2$ windows at the test wavelength divided by the transmission at that wavelength of the test sample (windows plus experimental specimen) divided by the thickness (t) of the test specimen.

To correct for the effect of multiple reflections, absorbance was determined using the relative change in the transmission of multiple liquid filled Harrick cells with differing cell spacer thicknesses. As many as 5 different optical path lengths were employed for a single determination of absorbance.

Harrick Cell Cleaning and Assembly Procedure

Prior to use, and after each sample run, the Harrick cell was flushed with Vertrel® XF fluorocarbon as a cleaning solvent (Miller-Stephenson Chemical Co., Danbury, Conn.). A clean 1 ml glass syringe (Becton Dickinson, Franklin Lakes N.J.) with a female Luer-Lock fitting was filled with Vertrel XF and then attached to the male Luer-Lock fitting on the Harrick cell, at which point the Vertrel XF was flushed through the cell. The cell was then blown dry using "house nitrogen" (produced from the boil off of liquid nitrogen, and containing fewer than 3 ppm of water and fewer than 5 ppm of oxygen). The cell was then disassembled in reverse order. The $CaF_2$ windows and Teflon® TFE spacers of desired thickness were placed into a 20 ml vial containing Vertrel® XF. The vials were capped and then put into an ultrasonic bath for 30–60 seconds. The $CaF_2$ windows and spacers were removed form the cleaning vial, given a final rub with a cotton swab moistened with Vertrel® XF then dried with air from a puffer bulb. The cell was then reassembled. The cleaning and assembly was done in air.

Loading the Harrick Cell in Air (Lab Hood)

To the cleaned cell, approximately 0.5 ml of the sample liquid was transferred from its container using a clean 1 ml Becton Dickinson (BD) glass syringe, the syringe was then attached into the cell and the cell was filled until the liquid meniscus was visible above the top Luer-Lok® fitting, so that no trapped bubbles were permitted to reside in the cell aperture. Then the top Luer-Lok® fitting on the Harrick cell was capped with the Teflon® TFE plug, and the cell was inverted with the syringe still attached. The syringe was twisted off and the exposed cell fitting was capped with another Teflon® TFE plug.

Loading the Harrick Cell in Nitrogen (Nitrogen Dry Box)

A cleaned and assembled cell was placed into either the nitrogen-purged antechamber of a Series 100 Plexiglas glove box (Terra Universal, Anaheim Calif.) or a previously nitrogen-flushed mini chamber attached to a nitrogen purged Nexus model 100043 dry box (Vacuum Atmospheres Co., Hawthorne, Calif.). The antechamber was continually purged with house nitrogen until the oxygen meter on the dry box read 10 ppm $O_2$ (approximately 30 minutes). The mini chamber was evacuated then filled with nitrogen three times prior to transfer to the dry box. The cell was loaded in the same manner as described above for loading in air.

Loading a Dried Sample into the Harrick Cell in Nitrogen (Nitrogen Dry Box)

A cleaned, assembled cell, with Teflon® TFE plugs (separate; not inserted), a clean 1 ml BD syringe and the selected sample that had been dried over adsorbents still in the sample bottle, were placed in the dry box described above in the manner described.

The sample bottle was opened and the liquid poured into a clean 15 ml BD syringe with a 0.45 micrometer PTFE Luer-Lok® filter. Using the syringe, the liquid was transferred through the filter into a clean, dry 20 ml vial. Approximately 0.5 ml of the filtered sample was transferred into the cell as described above.

Absorbance Determination

For the purpose of the examples herein, the absorbance of a material was determined using the relative transmission methods described above, for various cell thicknesses. The thickness of the test specimen was adjusted so that absorbance of at least 0.1% was achieved in order to keep measurement error the same across multiple specimens.

Absorbance was also measured directly using a Varian Cary 5 UV/Vis/NIR spectrometer. While single measurements in the Varian Cary 5 were not as accurate as relative transmission measurements using multiple path length measurements in a DUV-Vase® model V ellipsometer, data acquisition was much less time-consuming.

Index of Refraction Measurements

The index of refraction of a material and its temperature coefficient were determined using the minimum deviation prism method as described in Sinnock et al. Phys. Rev., 181 (3), p. 1297ff (1969) using the VUV-Vase® and the DUV-Vase® instruments (as in, for example, Burnett et al., "Absolute refractive indices and thermal coefficients of $CaF_2$, $SrF_2$, $BaF_2$, and LiF near 157 nm", Appl. Opt. 41, 2508–2513 (2002) and French et al., "Immersion Fluid Refractive Indices Using Prism Minimum Deviation Techniques", Optical Microlithography XVII, SPIE 5377–173, (2004).

A liquid-filled prism cell was used. The cell was a 60° equilateral, stainless steel, liquid prism, which included two 12.7 mm diameter×2 mm thick $CaF_2$ windows with Viton® polymer o-ring seals, and Luer-Lok® fittings for loading samples. The cell was disassembled for cleaning.

Prior to each use the cell was flushed with Vertrel® XF, through both Luer-Lok® fittings using a 1 ml BD glass syringe to flush out the previous specimen. Then the prism cell was dried with air from an air puffer bulb. The cell was then disassembled for cleaning. The $CaF_2$ windows and the stainless steel cell body were cleaned by ultrasonic agitation in closed vials containing Vertrel® XF for 30–60 seconds The $CaF_2$ windows were rubbed with a cotton swab wet with Vertrel® XF after removal from the ultrasonic bath, then dried with air from a puffer bulb. The cell body was removed from the cleaning bottle then dried with air from a puffer bulb. The cell was then reassembled.

Loading the Prism Cell in Nitrogen (Nitrogen Dry Box)

A cleaned, assembled cell, Teflon® TFE plugs, a clean 1 ml BD syringe and a sealed bottle of the selected sample material were placed into either the Series 100 Plexiglas Glove Box or the Nexus model 100043 Dry Box as described herein above.

The sample bottle was then opened and approximately 1 ml of the sample fluid was transferred from it (the fluid had been filtered through a 0.20 micron PTFE filter), following the method previously described herein above to minimize bubble formation.

When the sample was stored with an adsorbent, the liquid was poured into a clean 15 ml BD syringe with a 0.2 micrometer PTFE Luer-Lok® filter. Using the syringe, the liquid was transferred through the filter into a clean, dry 20 ml vial. Approximately 1 ml of the thus filtered sample was transferred into the cell as described above.

Minimum Deviation Index Method

The equilateral liquid prism was mounted on the VASE® which was equipped with a computer controlled, stepper motor driven ⊖-2⊖ angle-of-incidence stage. The sample rotation stage and the detector arm rotation stage were controlled separately during the measurement. For a given wavelength and incident angle, the detector arm was swept through a range of angles to determine the transmission angle. This process was repeated for a range of incident angles. Once the minimum deviation angle was determined, the index was determined according to the method of Sinnock et al., op.cit.

The VUV-VASE ellipsometer was used for index measurements at a nominal temperature of 32° C. The DUV-VASE ellipsometer was used for index measurements at a nominal temperature of 22° C.

The work described herein below was performed in glove bags, glove boxes and dry boxes. The glove bag was a polyolefin bag with glove shaped appendages provided for manipulation and a crude seal at the bottom made by folding. The glove box was a homemade box fabricated by gluing together sheets of PMMA boxes, and fitting out the box with regular dry box gloves. The dry box was a commercial box with high quality seals and ports. Applying Henry's law for oxygen concentrations as high as 100 ppm in nitrogen still results in only parts per billion-dissolved oxygen. There is no experimental evidence that the specific enclosure employed made a difference in results.

Comparative Example 1

The index of refraction of deionized water, with a conductivity of 17.5 megohm's at 32° C. was found to be 1.433 at 193 nm and 1.377 at 248 nm. The index of refraction, at 22° C. was found to be 1.436 at 193 nm and 1.378 at 248 nm.

Example 1

Preparation of Decahydro-2-trifluoromethyl-2,3,3-trifluoro-1,4:5,8-dimethanonaphthalene A 400 ml autoclave was charged with fresh distilled cyclopentadiene (110 g) and hexafluoropropylene (120 g, DuPont). The mixture was heated at 200° C. for 48 hours. The reaction mixtures from three identical reactions were combined and distilled at reduced pressure to give 5-trifluoromethyl-5,6,6-trifluorobicyclo[2,2,1]hept-2-ene (160.5 g, bp<47° C./0.4 Torr, yield 31%) and octahydro-6-trifluoromethyl-6,7,7-trifluoro-1,4:5,8-dimethanonaphthalene (268.6 g, bp 65–81° C./0.3 Torr, yield 40%).

A 400 ml autoclave was charged with octahydro-6-trifluoromethyl-6,7,7-trifluoro-1,4:5,8-dimethanonaphthalene (177 g, prepared as described above), methanol (100 ml, Burdick & Jackson, HPLC grade), and palladium on activated carbon (1 g containing 10% Pd, Alfa products, powder). The autoclave was closed and sealed, then shaken under 50 psig hydrogen pressure for 1 hour at room temperature. The hydrogen pressure was gradually increased to 200 psig over next hour at room temperature followed by 600 psig at 150° C. for 2 hour. After being cooled to room temperature, the reaction mixtures from two identical runs were combined and filtered to remove the catalyst. The filtrate was mixed with water (200 ml). The organic layer was isolated, diluted with methylene chloride (250 ml) and washed with water (100 ml), dried over Na2SO4 (EM Science, anhydrous granular). After removal of Na2SO4, the solution was distilled to remove the solvent and further distilled at reduced pressure Decahydro-2-trifluoromethyl-2,3,3-trifluoro-1,4:5,8-dimethanonaphthalene (269 g, bp 114–117° C./2 Torr, yield 75%). The fluid was transferred to a clean bottle (VWR, VWR® TraceClean™ bottle with TFE-lined closure) and purged with nitrogen. To the bottle was added activated silica gel (about ⅓ in volume of the fluid) in a dry box. The bottle was closed and shaken for about 30 seconds, then allowed to sit at room temperature for a few days. The fluid was decanted into another clean bottle and added activated silica gel (about ⅓ in volume of the fluid) in a dry box. Silica gel (Aldrich catalog number 24,982-3, type 3, 8 mesh) was dried at 500° C. for two hours before use. After a total three such silica gel treatments, the fluid was filtered through an Acrodisc® CR 25 mm syringe filter with 200 nm PTFE membrane (Pall Life Science). Its transparency was measured by the relative transmission method with 0.145, 0.4 and 0.6 cm path length and found to be 1.2 cm$^{-1}$ at 193 nm. It had a refractive index of 1.555 at 193 nm at the measurement temperature of 24° C.

Example 2

Preparation of Decahydro-2-trifluoromethyl-1,4:5,8-dimethanonaphthalene

A 400 ml autoclave was charged with octahydro-6-trifluoromethyl-1,4:5,8-dimethanonaphthalene (125 g, prepared as described in Example 1), methanol (100 ml, Burdick & Jackson, HPLC grade), and palladium on activated carbon (1 g containing 10% Pd, Alfa products, powder). The autoclave was closed and sealed, then shaken under 50 psig hydrogen pressure for 1 hour at room temperature. The hydrogen pressure was gradually increased to 200 psig over next hour at room temperature followed by 600 psig at 150° C. for 2 hour. After being cooled to room temperature, the reaction mixture was filtered to remove the catalyst. The filtrate was divided into two layers. The bottom layer was isolated and washed with water (2×50 ml), dried over Na$_2$SO4 (EM Science, anhydrous granular). After removal of Na2SO4, the liquid was distilled to give decahydro-2-trifluoromethyl-1,4:5,8-dimethanonaphthalene (92.3 g, bp 59–60° C./0.15 Torr, yield 73%). Further purification: About 40 g of decahydro-2-trifluoromethyl-1,4:5,8-dimethanonaphthalene was mixed with conc. sulfuric acid (5 ml). The resulting mixture was stirred at room temperature for 24 hours. The top layer was isolated and washed with NaHCO3 (0.5M), water, dried over Na2SO4. After removal of Na2SO4, the liquid was distilled to give a fluid. The fluid was transferred to a clean bottle (VWR, VWR® Trace-Clean™ bottle with TFE-lined closure) and purged with nitrogen. The bottle was added activated silica gel (about ⅓ in volume of the fluid) in a dry box. The bottle was closed and shaken for about 30 seconds, then allowed to sit at room temperature for a few days. The fluid was filtered through an Acrodisc® CR 25 mm syringe filter with 200 nm PTFE membrane (Pall Life Science). The filtered fluid had an absorbance 2.0 cm$^{-1}$ at 193 nm when measured by the cuvette method with a 0.1 cm path length. It had a refractive index 1.60 at 193 nm at the measurement temperature of 22° C.

Example 3

The apparatus employed for performing contact photolithography at 193 nm is depicted in FIG. 1. It consisted of a 193 nm Lambda-Physik (Ft. Lauderdale, Fla.) Optex ArF Excimer laser light source, a model D200 Scientech (5649 Arapahoe Avenue, Boulder, Colo. 80303) laser power meter, and an immersion fluid reservoir, all mounted on a 24" (61 cm)×18" (46 cm) optical table (Newport Corp., Irvine Calif.), positioned in a nitrogen flushed Nexus Dry Box (VAC Industries, Hawthorne Calif.) equipped with a trace oxygen analyzer and moisture probe (VAC Industries).

Test specimens were submerged 1 mm deep in the selected suitable polycyclic fluoroalkane in the reservoir as shown in FIG. 2. The laser beam traversed a distance of approximately 12" before being directed vertically downward towards the target surface as shown in FIG. 2. The target surface was a 100 mm diameter×0.5 mm thick silicon wafer mounted in a an aluminum holder. The holder was mounted on a rail so that the sample assembly could be translated horizontally. A manually controlled shutter was placed in the beam path as shown. An aluminum aperture plate, 9 cm×9 cm×0.3 cm with a 0.5×0.5 cm machined opening in the center was position into the beam path so as to select the most uniform section of the beam, 0.25 cm$^2$, for lithographic processing. The Scientech power meter, as shown, was used to measure the total exposure energy per unit area. After monitoring a consistent energy of typically 0.1 milliJoules per cm2, the sample holder was slid into place.

Immersion fluid was dispensed into the reservoir of FIG. 3 using a glass hypodermic syringe, (Popper & Sons inc., New Hyde Park N.Y.) with a chrome Luer-Lock tip. Attached to the tip was a 0.2-micrometer PTFE membrane syringe filter (Pall Gelman Laboratory, Ann Arbor, Mich.).

Sample Preparation

Single crystal silicon wafers, (Wafernet, Inc., San Jose Calif., 100 mm diameter×0 5 mm thick, polished on one side and having a natural oxide layer, approximately 2 nm thick, were prepared for 193 nm photolithography using the following procedure. The silicon wafers were coated in a YES-3 Vapor-Prime Oven (Yield Engineering Company, San Jose Calif.), with a layer of hexamethyldisilizane (HMDS) (Arch Chem. Ind, Norwalk, Conn.) used as an adhesion promoter for the photoresist.

The wafer was spin-coated with a photoresist polymer using a CEE Model 100CB Spinner/Hotplate (Brewer Science Inc., Derby England). The photoresist was a terpolymer of 1) tetrafluoroethylene (TFE), 2) a norbornene fluoroalcohol (NBFOH), and 3) t-butyl acrylate (t-BAc) as represented by the structure

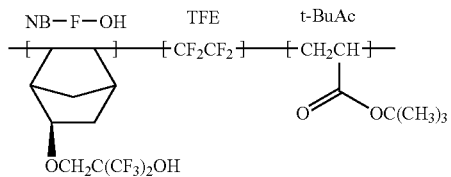

The polymer was prepared by free radical solution polymerization using peroxydicarbonate initiator and a hydrofluorocarbon solvent, as described in A. E. Feiring et al., "Design of Very Transparent Fluoropolymer Resists for Semiconductor Manufacture at 157 nm" Journal of Fluorine Chemistry, 122, 11–16, (2003). The photoresist polymer composition was 33% TFE, 43% NBFOH and 24% t-BA. The spinning solution for the formulated photoresist consisted of a 15 weight percent photoresist polymer dissolved in a 2-heptanone solvent with an additional 2 wt % of triphenylsulfonium nonaflate (TPS-Nf) present to serve as the photoacid generator (PAG) and 0.2 wt % of tetrabutylammonium lactate (TBALac) to serve as the contrast enhancing base additive The weight percent is by weight of the total, including the weight of the spinning solvent. For details of this resist formulation and processing see M. K. Crawford et al., "Single Layer Fluoropolymer Resists for 157 nm Photolithography at 157 nm exposure wavelength", Advances in Resist Technology and Processing XVIII, SPIE Vol. 5039, (2003), and also A. E. Feiring et al., op. cit.

Approximately 1 ml of the photoresist solution so prepared was dispensed through a 0.2 micrometer polytetrafluoroethylene syringe filter onto the HMDS vapor primed coated wafer and the wafer was spun-coated at 2500 rpm for 60 seconds in air and then a post apply bake (PUB) of the resist was done at 150° C. for 60 seconds The photoresist films were visually inspected and the thickness of each film measured using a Filmetrics film thickness instrument (Filmetrics Inc., San Diego Calif.).

1 ml of Teflon® TFE-AF (The DuPont Company) was dispensed onto the photoresist-coated wafer and the wafer was spun at 2500 rpm for 1 minute. The sample was then transferred into the VAC Dry Box and placed into the sample holder.

A contact mask was formed using SPI Copper TEM Grids, (SPI Inc. West Chester Pa.), 3 mm diameter×50 mesh, with a lateral periodicity of 500 micrometers, and line widths of 100 microns by placing the grids end to end across the entire wafer in the beam exposure path. The photoresist coated wafer was immersed to a fluid depth of approximately 1 mm by dispensing approximately 20 milliters of suitable polycyclic fluoroalkane through a glass syringe with a 0.2 micron filter over the entire 100 mm diameter of the top coat/photoresist/HMDS primed silicon wafer.

Sequential exposure was effected by physically translating the wafer into the exposure zone by ½ cm increments along a slide rail mounted on the optical table thereby providing a series of ½ cm strips of increasing dosage. After exposure the suitable polycyclic fluoroalkane was pipetted off and the contact masks were removed. The exposed wafer was then transferred out of the VAC Dry Box and post-exposure baked at 135° C. for 60 seconds in air on the CEE Model 100CB Hotplate. The Top Coat was then removed from the wafer by spin cleaning on the CEE Model 100CB spinner, by dispensing FC-75 solvent over the top surface of the wafer, then spinning the wafer at 2500 rpm for 60 seconds in air. The thus exposed photoresist was then developed using Shipley LDD-26W Developer (Shipley Company, L.L.C., Marlborough Mass.), by immersion in the developer for 60 seconds at room temperature, in air. Then the sample was immersed in deionized (D.I.) water for 10 to 15 seconds, removed from the water bath, rinsed with a D.I. water spray and blown dry with nitrogen gas.

The dried samples were visually and microscopically inspected to determine the contact print dose, E1 Dry, which refers to the minimum exposure energy required for image formation in the absence of an immersion liquid, and the contact print dose E1 Wet, which refers to the minimum exposure energy required for image formation in the presence of a given immersion liquid.

Example 3A

The photoresist layer prepared as described above was 260 nm thick. The photoresist layer was coated with a topcoat as described above. The topcoat solution was prepared by combining 4.1 wt-% Teflon® TFE-AF 1601 in FLUORINERT™ FC-75. The topcoat layer so prepared was 200 nm thick. This wafer, dry (without immersion fluid), was then exposed to 193 nm light. E1 Dry, the exposure dose required to clearly transfer the TEM Copper grid image onto the photoresist was found to be 3.2 mJ/cm². A photomicrograph of the result is shown in FIG. 5.

Example 3B

The procedure of Example 3A was repeated except that the immersion fluid of Example 1 was used, Decahydro-2-trifluoromethyl-2,3,3-trifluoro-1,4:5,8-dimethanonaphthalene, with an optical absorbance of 1.36/cm at a fluid thickness of 1 milliter. E1 Wet, the exposure dose required to clearly transfer the TEM Copper grid image onto the photoresist, was found to be 3.6 mJ/cm². A photomicrograph of the result is shown in FIG. 4.

Example 4

Preparation of a Non-Fluorinated Model Compound

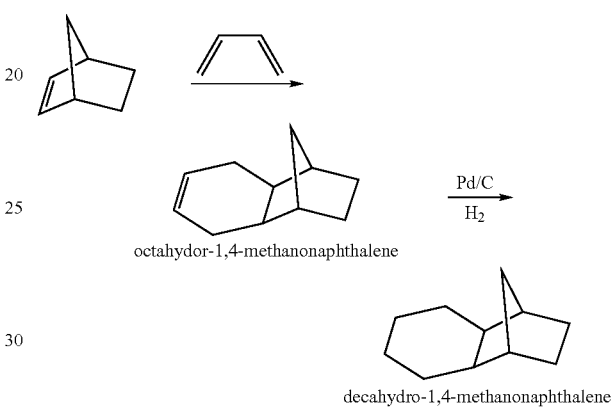

octahydor-1,4-methanonaphthalene decahydro-1,4-methanonaphthalene

Preparation of decahydro-1,4-methanonaphthalene

Step one: Preparation of octahydro-1,4-methanonaphthalene

A 400 ml autoclave was charged with bicyclo[2,2,1]-2-heptene (152 g, Aldrich), 4-methylphenol (1 g, Aldrich), and butadiene (110 g). The mixture was heated at 200° C. for 10 hours. The reaction mixtures from four identical reactions were combined and distilled at atmosphere to give starting bicyclo[2,2,1]-2-heptene (307 g). Further distillation at reduced pressure afforded octahydro-1,4-methanonaphthalene (349 g with 97–98% purity, bp 47° C./0.05 Torr, yield 73%, based on consumed bicyclo[2,2,1]-2-heptene) and about 120 g of product with lower purity (bp 47° C./2 Torr to 58° C./0.16 Torr).

Step two: Preparation of decahydro-1,4-methanonaphthalene

A 400 ml autoclave was charged with octahydro-1,4-methanonaphthalene (122 g, prepared as described above), methanol (100 ml, Burdick & Jackson, HPLC grade), and palladium on activated carbon (1.5 g containing 10% Pd, Alfa products, powder). The autoclave was closed and sealed, then shaken under 50 psig hydrogen pressure for 20 minutes at room temperature. The hydrogen pressure was increased to 200 psig for 10 minutes at room temperature followed by 600 psig at 70° C. for 45 minutes. The reaction mixtures from three identical reactions were combined and filtered to remove the catalyst. The filtrate separated into two layers. The MeOH layer (top layer) was isolated and concentrated to give a residue, which was combined with product layer (the bottom layer). The combined crude product was distilled at reduced pressure to give decahydro-1,4-methanonaphthalene (318.6 g, bp 71–73° C./0.2 Torr, yield 86%).

Example 5

Preparation of decahydro-2-trifluoromethyl-1,4-methanonaphthalene

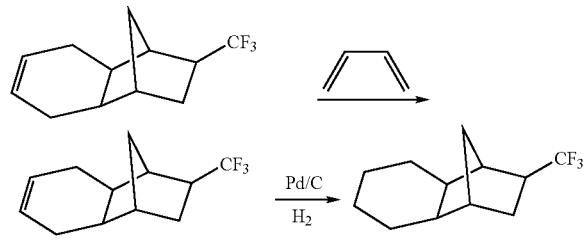

Step one: Preparation of octahydro-trifluoromethyl-1,4-methanonaphthalene

A 400 ml autoclave is charged with 5-trifluoromethylbicyclo[2,2,1]-2-heptene (262 g, preparation is included in example 1 of CL 2910), 4-methylphenol (1 g), and butadiene (110 g). The mixture is heated at 200° C. for 10 hours. The octahydro-2-trifluormethyl-1,4-methanonaphthalene product is purified by distillation at reduced pressure.

Step two: Preparation of decahydro-2-trifluoromethyl-1,4-methanonaphthalene

A 400 ml autoclave is charged with 177 g of the thus purified octahydro-2-trifluormethyl-1,4-methanonaphthalene, methanol (100 ml, Burdick & Jackson, HPLC grade), and palladium on activated carbon (1.5 g containing 10% Pd, Alfa products, powder). The autoclave is closed and sealed, then it is shaken under 50 psig hydrogen pressure for 20 minutes at room temperature. The hydrogen pressure is increased to 200 psig for 10 minutes at room temperature followed by 600 psig at 70° C. for 45 minutes. The decahydro-2-trifluoromethyl-1,4-methanonaphthalene product is purified by distillation at reduced pressure. The crude product is treated with sulfuric acid as described in Example 2.

Comparative Example 2

The same procedures were followed as in Example 3A except in this case no immersion fluid and no topcoat were used. The photoresist layer was 246 nm thick. E1 was found to be 1.2 mJ/cm² was required to effect clean image formation in the photoresist.

What is claimed is:

1. A polycyclic fluoroalkane compound represented by the formula

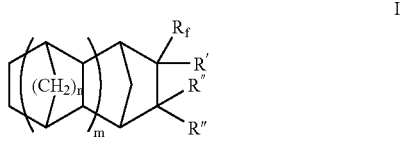

I where $R_f$ is a fluorinated alkyl of 1–10 carbons that is linear, branched, or cyclic; R' is H, F, an alkyl of 1–10 carbons that is linear, branched, or cyclic; a fluorinated alkyl I of 1–6 carbons that is linear, branched, or cyclic; each R" is independently H or F; n=0 or 1; and, m=1 or 2 provided that m is not 2 when n=0.

2. The compound of claim 1 wherein n=1 and m=1.

3. The compound of claim 1 wherein both R" are F.

4. The compound of claim 1 wherein R' is F.

5. The compound of claim 1 wherein $R_f$ is perfluoromethyl or perfluoroethyl.

6. The compound of claim 5 wherein $R_f$ is perfluoromethyl.

7. The compound of claim 1, having a F/H ratio of 0.5 or less.

8. A composition comprising a compound of claim 1 and having a concentration of oxygen below 1 ppm.

9. The composition of claim 8, having an absorbance at 193 nm of 2 cm$^{-1}$ or lower.

10. The composition of claim 8, having a refractive index at 193 nm of at least 1.50.

11. The compound of claim 1 wherein R' is F, each R" is F, n=1, m=1, and Rf is perfluoromethyl.

12. A composition comprising the compound of claim 11 and having a concentration of oxygen below 1 ppm.

13. The composition of claim 12 wherein having an absorbance at 193 nm of 2 cm$^{-1}$ or lower.

14. The composition of claim 12, having a refractive index at 193 nm of at least 1.50.

* * * * *